United States Patent
Patwardhan

(10) Patent No.: US 11,769,265 B2
(45) Date of Patent: *Sep. 26, 2023

(54) SKIN ASSESSMENT USING IMAGE FUSION

(71) Applicant: Canfield Scientific, Incorporated, Parsippany, NJ (US)

(72) Inventor: Sachin V. Patwardhan, Mount Tabor, NJ (US)

(73) Assignee: Canfield Scientific, Incorporated, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/503,335

(22) Filed: Oct. 17, 2021

(65) Prior Publication Data

US 2022/0039657 A1   Feb. 10, 2022

Related U.S. Application Data

(63) Continuation of application No. 16/894,828, filed on Jun. 7, 2020, now Pat. No. 11,154,200, which is a
(Continued)

(51) Int. Cl.
*H04N 7/18*   (2006.01)
*G06T 7/42*   (2017.01)
(Continued)

(52) U.S. Cl.
CPC .............. *G06T 7/42* (2017.01); *A61B 5/0077* (2013.01); *A61B 5/442* (2013.01); *G06F 18/00* (2023.01);
(Continued)

(58) Field of Classification Search
CPC .......... G06K 9/00; H04N 7/18; H04N 5/2256; A61B 5/0077; A61B 5/442; A61B 5/0075;
(Continued)

(56) References Cited

U.S. PATENT DOCUMENTS 7,167,244 B2 * 1/2007 Mullani ................. A61B 5/445
356/369
8,498,460 B2 * 7/2013 Patwardhan ........... A61B 5/441
382/128
(Continued)

OTHER PUBLICATIONS

Steven L. Jacques et al. "Imaging skin pathology with polarized light" Journal of Biomedical Optics, vol. 7 No. 3, 329-340 (Jul. 2002) (Year: 2002).*

*Primary Examiner* — Trang U Tran

(57) ABSTRACT

Apparatuses and methods are disclosed for assessing the texture of skin using images thereof. In exemplary embodiments, a texture map of an area of skin is generated from a combination of a parallel-polarized image and a cross-polarized image of the area of skin. The texture map is then flattened to remove the underlying curvature of the skin. A texture roughness metric is then generated based on the flattened texture map. An image of the texture map and the metric can be displayed to provide visual and alphanumeric representations of the texture of skin, thereby facilitating the comparison of baseline and follow-up images of the skin, such as those taken before and after treatment.

20 Claims, 7 Drawing Sheets

Related U.S. Application Data continuation of application No. 16/402,149, filed on May 2, 2019, now Pat. No. 10,702,160.

(60) Provisional application No. 62/666,022, filed on May 2, 2018.

(51) Int. Cl.

| | | |
|---|---|---|
| *A61B 5/00* | (2006.01) | |
| *G06T 7/30* | (2017.01) | |
| *G06T 7/174* | (2017.01) | |
| *G06F 18/00* | (2023.01) | |
| *H04N 23/56* | (2023.01) | |
| *G06T 7/00* | (2017.01) | |

(52) U.S. Cl.
CPC ............... *G06T 7/174* (2017.01); *G06T 7/30* (2017.01); *H04N 23/56* (2023.01); *A61B 5/0075* (2013.01); *A61B 5/443* (2013.01); *G06T 7/0012* (2013.01); *G06T 2207/10152* (2013.01); *G06T 2207/20064* (2013.01); *G06T 2207/20212* (2013.01); *G06T 2207/30088* (2013.01); *G06T 2207/30196* (2013.01)

(58) Field of Classification Search
CPC ............. A61B 5/443; G06T 7/42; G06T 7/30; G06T 7/174; G06T 7/0012; G06T 2207/10152; G06T 2207/20212; G06T 2207/30088; G06T 2207/30196
USPC .................................. 382/128, 103; 348/77
See application file for complete search history.

(56) References Cited

U.S. PATENT DOCUMENTS

| | | | | |
|---|---|---|---|---|
| 9,101,320 | B2 * | 8/2015 | Cummins | ............ A61B 5/0077 |
| 10,244,991 | B2 * | 4/2019 | Shademan | .............. G16Z 99/00 |
| 2007/0229658 | A1 * | 10/2007 | Kanamori | ................ G06T 3/40 |
| | | | | 348/207.99 |

* cited by examiner

SKIN ASSESSMENT USING IMAGE FUSION

RELATED APPLICATIONS

This application is a continuation of and claims the benefit under 35 U.S.C. § 120 of U.S. patent application Ser. No. 16/894,828 filed Jun. 7, 2020, which is incorporated herein by reference in its entirety and which is a continuation of and claims the benefit under 35 U.S.C. § 120 of U.S. patent application Ser. No. 16/402,149 filed May 2, 2019, which is incorporated herein by reference in its entirety and which claims priority from U.S. Provisional Patent Application No. 62/666,022 filed May 2, 2018, also incorporated herein by reference in its entirety.

BACKGROUND INFORMATION

The present disclosure relates to image processing and analysis, particularly the assessment of the texture of skin, such as the facial skin of humans.

In selecting medical or cosmetic treatments or products to be applied to human skin, it is helpful to assess the condition of the skin, before, during and after such applications. A condition of the skin that is often of interest is the texture of the skin, which is typically assessed by human observation. Whether made by the subject or even a professional, such an observation-based assessment, however, is largely subjective, difficult to quantify, and prone to wide variability. Additionally, some time and effort is required on the part of the observer to make, communicate, and record their assessment. The aforementioned issues are particularly problematic, for example, in studies where products or treatments are applied to large numbers of subjects and the efficacy thereof is to be assessed.

Facial skin texture is a combination of features (pores, bumps, etc.) that make up the overall surface topography in non-wrinkled areas of the face, like areas of the cheek, for example. Texture does not include color components, pigment information, underlying curvature or structure, and lighting gradients. Such features further complicate the objective assessment of skin texture.

SUMMARY OF THE DISCLOSURE

The present disclosure also sets out an apparatus comprising: a storage device configured to store instructions; and a processor configured to execute instructions stored in the storage device to: obtain a parallel-polarized image of the skin area; obtain a cross-polarized image of the skin area; generate a texture map from a combination of the parallel-polarized and cross-polarized images; generate at least one of a texture map image or a texture metric from the texture map; and cause the at least one of the texture map, the texture map image, or the texture metric to be displayed, stored, communicated, or processed.

The present disclosure also sets out a method comprising: obtaining a parallel-polarized image of the skin area; obtaining a cross-polarized image of the skin area; generating a texture map from a combination of the parallel-polarized and cross-polarized images; generating at least one of a texture map image or a texture metric from the texture map; and causing the at least one of the texture map, the texture map image, or the texture metric to be displayed, stored, communicated, or processed.

These and other aspects of such apparatuses and methods and exemplary variants thereof are described in greater detail below.

BRIEF DESCRIPTION OF THE DRAWINGS

A more complete understanding of the present disclosure may be realized by reference to the accompanying drawings.

DETAILED DESCRIPTION

Figure 1:
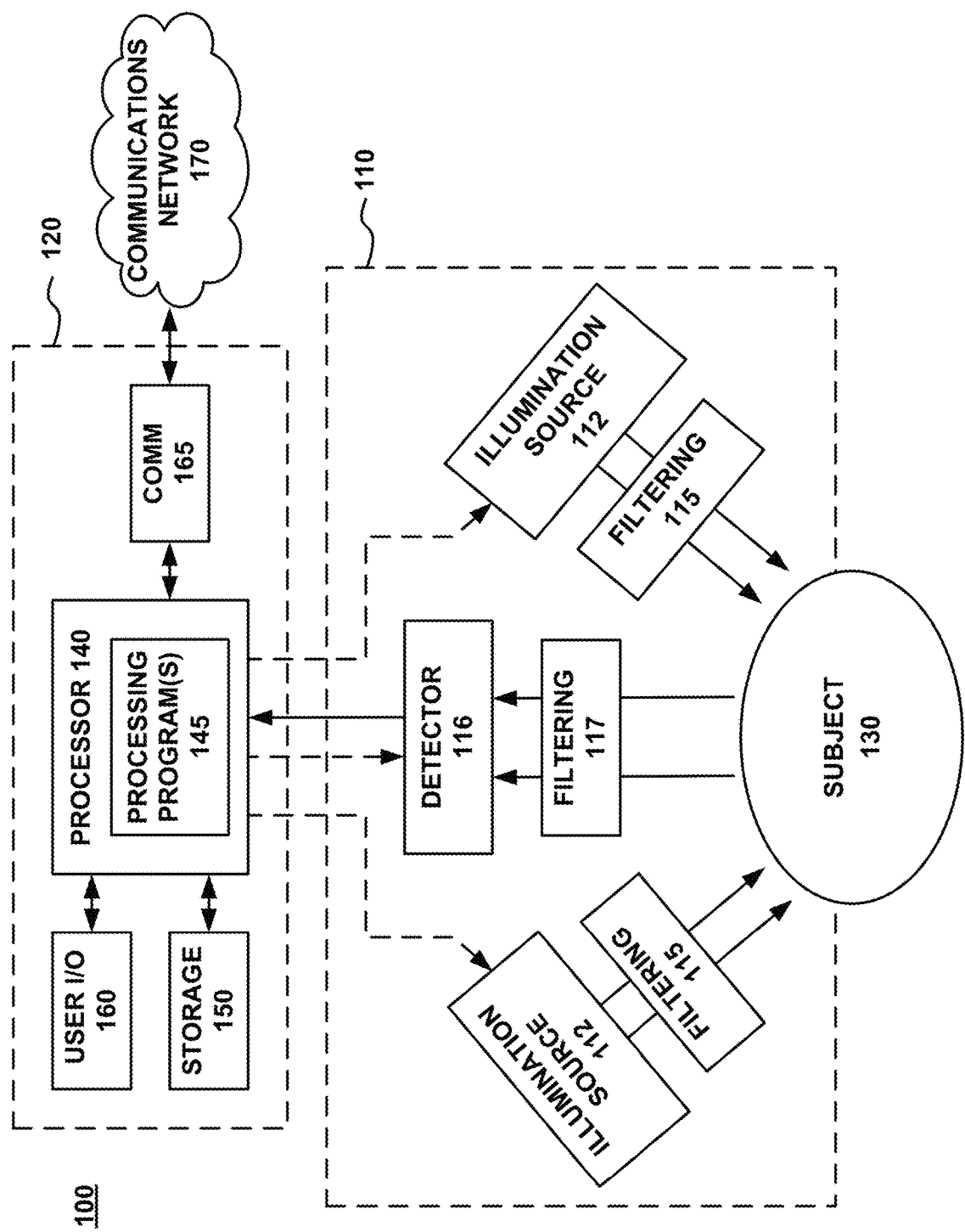
FIG. 1 is a schematic representation of an exemplary system in accordance with the present disclosure.

The following merely illustrates the principles of the disclosure. It will thus be appreciated that those skilled in the art will be able to devise various arrangements which, although not explicitly described or shown herein, embody the principles of the disclosure and are included within its spirit and scope. More particularly, while numerous specific details are set forth, it is understood that embodiments of the disclosure may be practiced without these specific details and in other instances, well-known circuits, structures and techniques have not been shown in order not to obscure the understanding of this disclosure.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently-known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the invention.

In addition, it will be appreciated by those skilled in art that any flow charts, flow diagrams, and the like represent various processes which may be substantially represented in computer readable medium and so executed by a computer or processor, whether or not such computer or processor is explicitly shown.

The functions of the various elements shown in the drawings, including any functional blocks, steps, procedures, modules, units or the like may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, dedicated circuitry, digital signal processor (DSP) hardware, network-based processors, application specific integrated circuitry (ASIC), read-only memory (ROM), random access memory (RAM), and non-volatile storage. Other hardware, conventional and/or custom, may also be included.

Software modules, or simply modules which are implied to be software, may be represented herein as any combination of flow chart elements or other elements indicating performance of process steps and/or textual description. Such modules may be executed by hardware that is expressly or implicitly shown.

As used herein, the term "image" may encompass any form of photo-documentation, including 2D images and/or 3D surfaces and/or 3D volumetric image data, where a 2D image could be a single or a multichannel visible impression obtained by a camera, a 3D surface could be points in a 3D space connected by line segments to form a polygonal mesh along with any associated 2D images that represent the underlying texture and a 3D volumetric image data might represent a stack of 2D images that represent a 3D volume of the object being imaged, such as a stack of MRI images.

FIG. 1 schematically depicts an exemplary system 100 in accordance with the present disclosure for assessing the texture of human skin. As shown in FIG. 1, components of system 100 include an image capture system 110 coupled with a processing system 120. Image capture system 110 may include one or more hand-held or mounted point-and-shoot or DSLR cameras, mobile cameras, frontal or rear-facing smart-device cameras, dermatoscopes (e.g., Canfield Scientific Inc.'s VEOS), 2D skin imaging systems (e.g., Canfield Scientific Inc.'s VISIA, VISIA-CR), 3D human body imaging devices (e.g., Canfield Scientific Inc.'s VECTRA), Canfield Scientific Inc.'s NEXA system, 3D Total Body systems (e.g., Canfield Scientific Inc.'s WB360), and/or 3D volumetric imaging devices, among others.

In exemplary embodiments, image capture system 110 includes one or more illumination sources 112 which are activated to shine light onto a subject's skin 130 through a respective filtering element 115. Light reflected or emitted from the subject tissue 130 is captured by a detector 116 through a filtering element 117. Each filtering element 115, 117 may include one or more filters for passing or blocking light of a selected wavelength or band of wavelengths, and/or polarizers, collectively "filters," which can be selectively placed in or out of the respective optical path of the filtering element. In exemplary embodiments, detector 116 may comprise a camera, such as a conventional digital SLR camera or the like, a digital video camera, or multiple one- or two-dimensional detectors, with similar or different characteristics. Multiple detectors 116 can be arranged to capture two- or three-dimensional images.

Advantageously, the captured images can be single mode or multimodal—including, for example, those from standard white light, polarized light, and/or fluorescent light—captured at selected wavelengths and/or illuminated with selected wavelengths of light. Note that the term "light" as used herein is not necessarily limited to humanly visible electromagnetic radiation, and may include portions of the electromagnetic spectrum outside the visible range.

Images captured by image capture system 110 are provided to processing system 120 for processing as described below. Of further advantage, processing system 120 may also control image capture system 110, for example, by controlling one or more aspects of the image capture and/or illumination of the subject, such as exposure, modality, or filtering, among others.

Images may also be provided to processing system 120 from other sources and by other means. For example, images may be provided via communications network 170, or in a non-transient, computer-readable storage medium, such as storage 150.

Processing system 120 includes a processor 140 that may be coupled to storage 150, for storing and retrieving images, among other data, and to input/output devices 160, such as a display device and/or user input devices, such as a keyboard, mouse, touchscreen, or the like. Processor 140 may also be coupled to a communications module 165 for interconnection with a communications network 170, such as the Internet, for transmitting and receiving images and/or data, and/or receiving commands, software updates or the like. Processing system 120 may be implemented, for example, with one or more central processing units, computers, workstations, PCs, tablet computers or the like, operating in accordance with one or more programs 145 embodied in a compatible, non-transient, computer-readable storage medium. The interface between image capture system 110 and processing system 120 can be wired, wireless, direct, or indirect (e.g., via a network, Internet.)

It should be noted that the exemplary system 100 illustrates just one of a variety of possible arrangements contemplated by the present disclosure. For example, the various elements of system 100 need not be co-located. For example, image capture system 110 and I/O devices 160 can be located in a dermatologist's office and processor 140 and storage 150 can be remotely located, functioning within a tele-dermatology framework, or may be "cloud-based," interacting with image capture system 110 and I/O devices 160 over communications network 170. In other exemplary arrangements, I/O devices 160 can be remotely located from image capture system 110, thereby allowing a user to remotely examine subjects' images.

Figure 2:
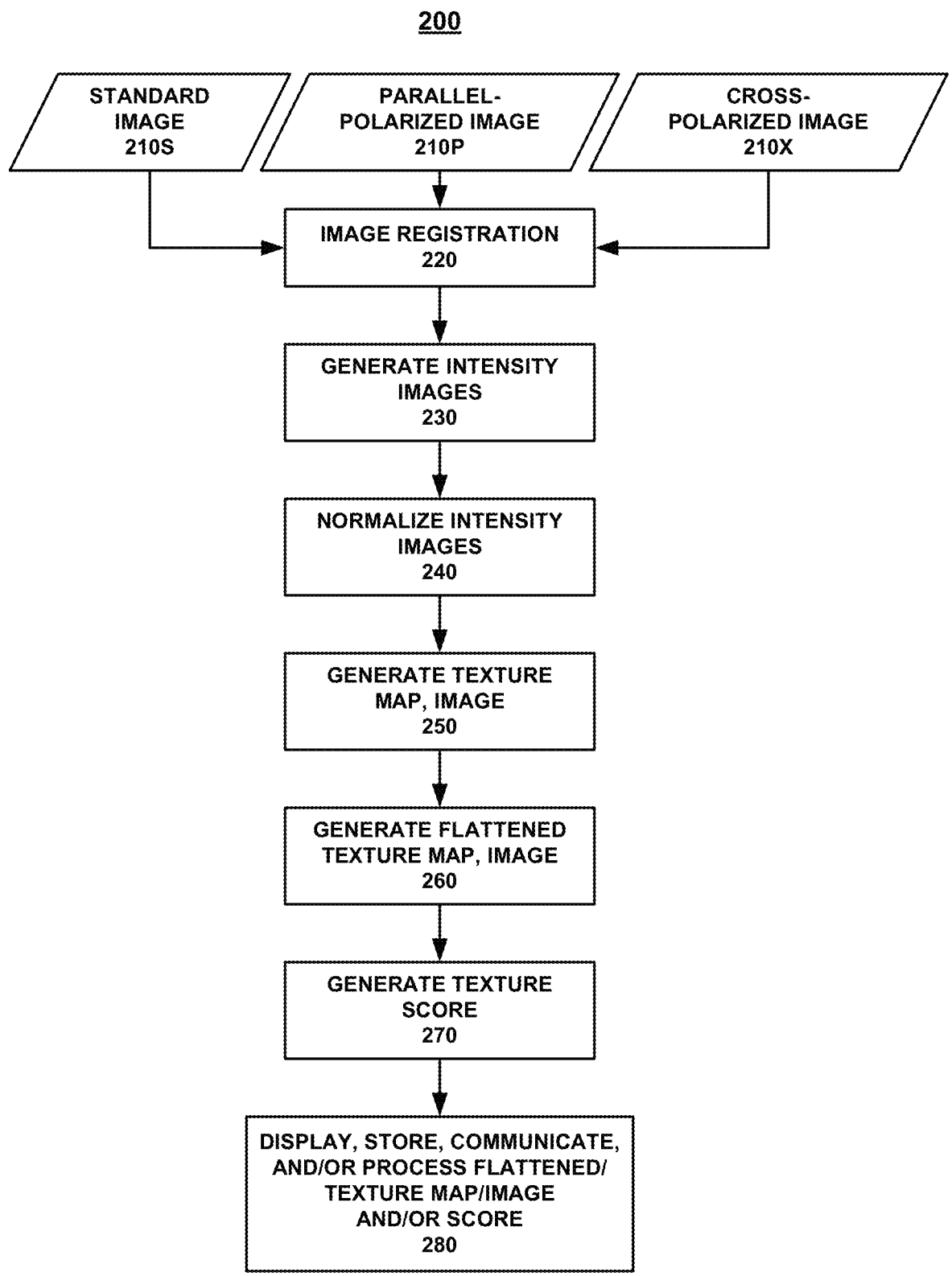
FIG. 2 is a flow chart depicting an exemplary method in accordance with the present disclosure.

FIG. 2 is a flowchart depicting an exemplary process 200, such as would be carried out with exemplary system 100 in accordance with the present disclosure. It is contemplated that in carrying out exemplary process 200, the system 100 operates in accordance with program(s) 145 executed by processor 140.

As shown in FIG. 2, operation begins by obtaining a standard image 210S, a parallel-polarized image 210P, and a cross-polarized image 210X. Input images 210 can be obtained by being captured, such as with image capture system 110, or provided to system 100 such as via communications network 170, in storage 150, or by any other suitable means.

Figure 3C:
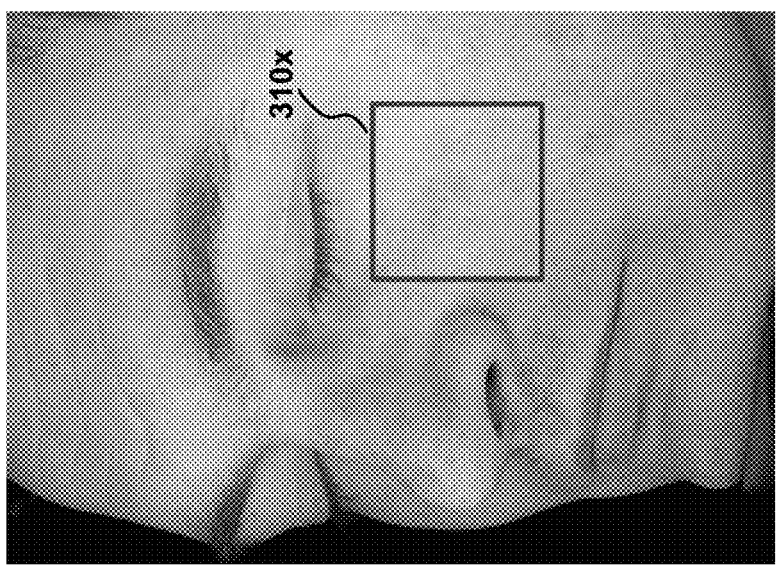
FIGS. 3A-3C show illustrative standard, parallel-polarized, and cross-polarized images, respectively, as obtained for the exemplary method of FIG. 2.
Figure 3B:
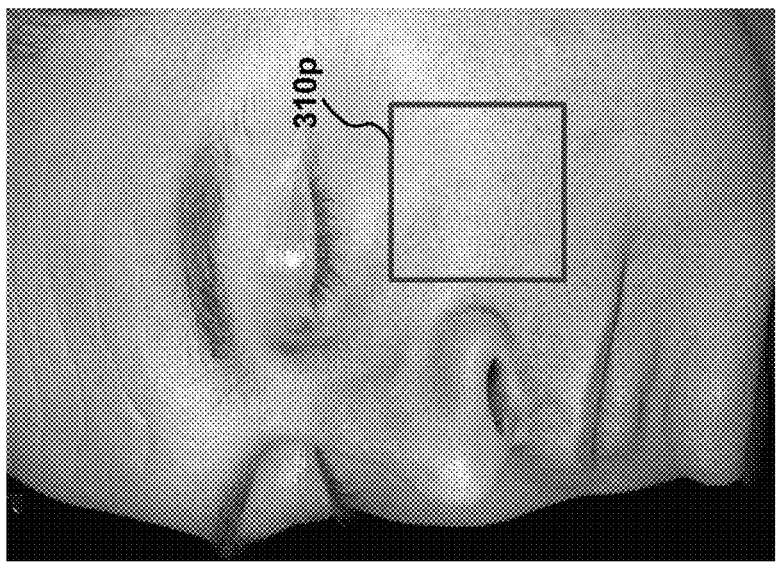
Figure 3A:
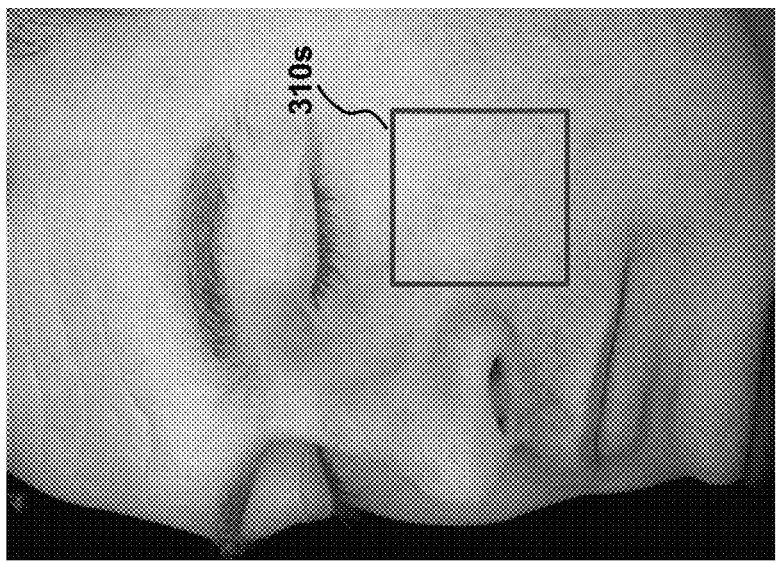

In capturing standard image 210S, the subject 130 is illuminated with broad-spectrum, unpolarized white light and an RGB image of the subject thus illuminated is captured without polarizing filters. An illustrative standard image is shown in FIG. 3A.

In capturing parallel-polarized image 210P, the subject 130 is illuminated with light that is linearly polarized with a given orientation and an RGB image of the subject thus illuminated is captured through a linear polarized filter of the same orientation. An illustrative parallel-polarized image is shown in FIG. 3B.

In capturing cross-polarized image 210X, the subject 130 is illuminated with light that is linearly polarized with a given orientation and an image of the subject thus illuminated is captured through a linear polarized filter of an orientation orthogonal to that of the illuminating light. An illustrative cross-polarized image is shown in FIG. 3C.

Although broad-spectrum (white light) illumination can be used, because imaging skin texture does not entail looking deeply into the skin, a shorter wavelength spectral-band illumination, including monochromatic illumination, can also be used in implementations consistent with the present disclosure. Longer wavelength illumination, such as in the red band, which can penetrate to greater skin depths, can be avoided. Additionally, while linear polarization is described, circular polarization can also be used.

Preferably, the images 210 are captured using flash illumination and in temporal proximity to each other, with the subject stationary so as to avoid or minimize the effects of any movement or changes in the subject's pose. Note that the images 210 are of the same area of the subject's face, with the same pose, and captured from the same angle. Additionally, to maintain consistency between images, the same illumination source(s) are preferably used for both images, with polarization of the illumination provided, for example, using a polarizer that can be rotated to the desired orientation for each image, a filter wheel, or other suitable arrangement allowing illumination of orthogonal polarizations to be selectively emitted from the same point(s). Alternatively, the same illumination polarization can be used for both parallel- and cross-polarized images, and the polarizer in front of the camera rotated or changed. Moreover, the image capture parameters used to capture each image are preferably set to ensure that there will be no saturation (e.g., "hot-spots") in the captured images.

The input images 210 are preferably captured in a controlled environment, such as with a Canfield Scientiific VISIA-CR system, to ensure uniform illumination over the skin surface being imaged. In any case, however, for best results it may be desirable to correct the images for non-uniform illumination against an image of a white standard target. For images captured with non-uniform illumination, it may be desirable to limit analysis to those portions of the imaged skin surface that are generally flat and parallel to the camera sensor, such as the forehead in a front view or the cheeks in a side view of a subject's face. Color correction and other suitable pre-processing of the input images 210 may also be performed.

After the input images 210 have been obtained, they are subjected to image registration at 220. In an exemplary such operation, images 210 are elastically or non-elastically registered based on facial landmarks (e.g., corners of eyes, lips, nose, etc.) and skin features (e.g., pores, wrinkles, moles, birthmarks, etc.) to remove any movement artifacts due to movement that may have occurred between images, particularly if the images were taken at different points in time.

After registration at 220, an intensity image is generated at 230 for each of the RGB input images 210, as modified by the registration operation (and/or any other corrective processing). In exemplary implementations, the intensity image can be generated by calculating, for each pixel, an intensity value as the mean of the corresponding Red, Green and Blue component values for each pixel; i.e., I=(R+G+B)/3. Alternatively, a particular one of the color channels can be used, preferably the Green channel of each of the input images 210. The Green channel shows absorption due to both hemoglobin and melanin in the cross-polarized image. In generating a texture map, as described below, it is such absorption which it is desired to remove. Moreover, for typical RGB camera sensors the Green channel has better sensitivity than the Blue and Red channels.

The three intensity images generated at 230 are then normalized at 240 with respect to a respective maximum intensity value determined for each of the intensity images. In exemplary implementations, this generally entails dividing the pixel intensity values determined at 230 for each image by the image's respective maximum intensity value, thereby converting the pixel intensity values for each image to a range of 0 to 1.

In performing the normalization for each of the intensity images at 240, those pixels representing non-skin features, such as hair and eyes, are excluded. Additionally, to reduce the effects of noise, the images are preferably filtered. Moreover, because the maximum intensity value may be due to an isolated pixel, using a histogram of intensity distribution to perform the normalization is advisable. More specifically, in an exemplary embodiment, a high-end percentile and a low-end percentile of a histogram of the intensity distribution of each intensity image are selected and used for scaling and normalizing the respective intensity image. For example, all pixels with intensity lower than the $5^{th}$ percentile intensity value (P5) are made equal to the $5^{th}$ percentile intensity value and all pixels with intensity above the $95^{th}$ percentile intensity value (P95) are made equal to the $95^{th}$ percentile intensity value. As thus modified, the minimum intensity of an intensity image will be the $5^{th}$ percentile intensity value (P5) and the maximum intensity of the image will be the $95^{th}$ percentile intensity value (P95). The normalized/scaled intensity image I' can then be obtained from the intensity image I in accordance with the following relationship:

$$I'=(I-P5)/(P95-P5). \quad (1)$$

Operation then proceeds to 250 in which a texture map is generated from the standard, parallel-polarized, and cross-polarized intensity images as normalized at 240. In exemplary implementations, a texture map is generated by dividing the normalized parallel-polarized intensity image by the normalized cross-polarized intensity image and then adding a fraction of the normalized standard intensity image to the result. Such an operation can be expressed as follows:

$$T=P/X+\alpha S, \quad (2)$$

where T is the normalized intensity of each texture map pixel, P, X and S are the normalized intensities of the corresponding pixels in the parallel-polarized, cross-polarized, and standard intensity images, respectively, and a is a parameter having a value between 0 and 1.

In exemplary implementations, parameter α has a typical range of 0 to 0.5. If the skin area of interest is almost flat (such as the forehead in a front view image, for example) then parameter α can be set to zero. On curved surfaces, parameter α can be set so as to add a fraction of the normalized intensity S of the standard image to preserve the curvature appearance for a visual evaluator.

A flattened texture map, i.e., a texture map with facial curvature removed, can be generated at 260 by subtracting a large-size gaussian filtered texture map from a small-size gaussian filtered texture map. The filter sizes can be selected based on image resolution and the size(s) of texture feature(s) to be preserved in the flattened texture map.

Figure 4A:
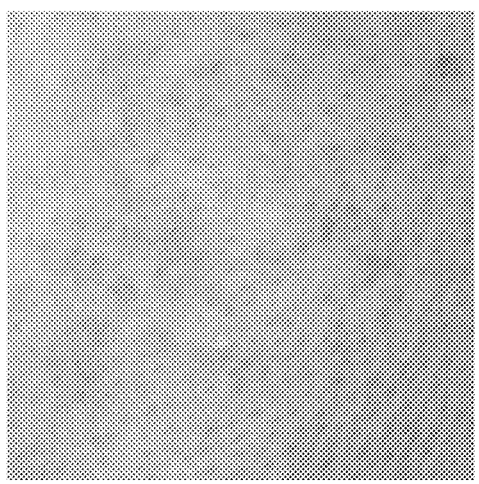
FIGS. 4A-4C show enlarged images of a portion of the skin shown in the images of FIGS. 3A-3C.
Figure 4B:
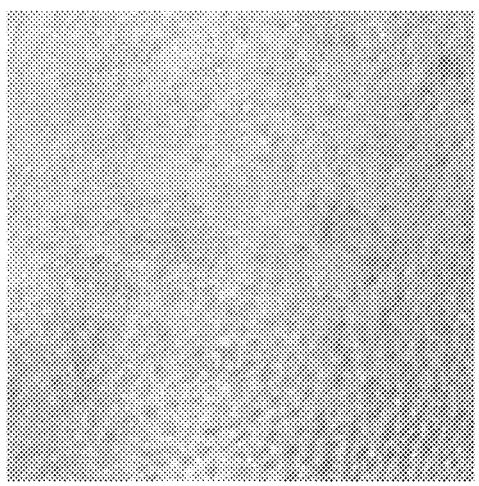
Figure 4C:
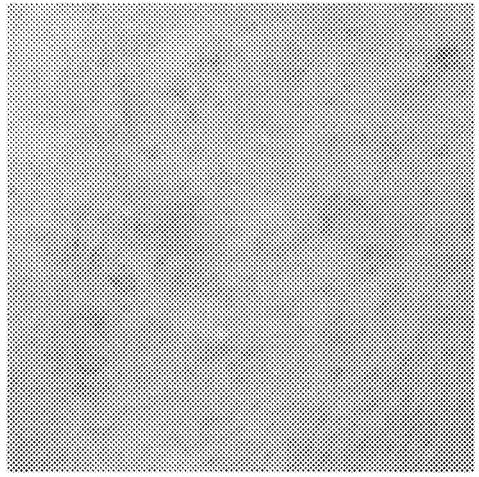
Figure 4D:
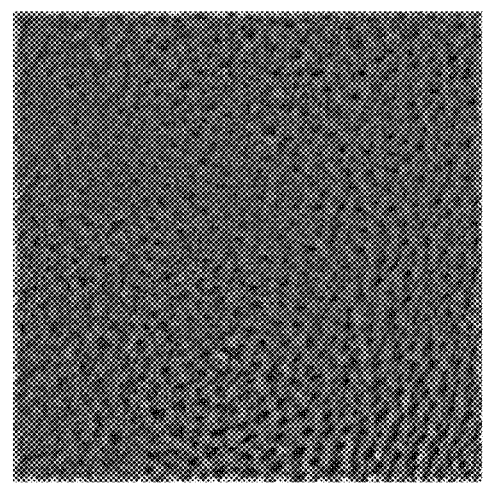
FIG. 4D shows a flattened texture map generated therefrom in accordance with the method of FIG. 2.

The flattened normalized texture map generated at 260 can be scaled to gray level values (e.g., 0-255) to generate a texture map image, which can be displayed. An illustrative such grayscale texture map image is shown in FIG. 4D, with the corresponding standard, parallel-polarized, and cross-polarized images shown in FIGS. 4A-4C, respectively. As indicated, the images of FIGS. 4A-4C are of respective portions 310*s*, 310*p* and 310*x* of the images of FIGS. 3A-3C. An image of the texture map generated at 250, before flattening, may also be generated, instead of or in addition to the flattened texture map image.

The flattened texture map image, such as that of FIG. 4D, thus shows the selected portion of the skin surface without glare, pigmentation, color, or the curvature of the face underlying the selected portion of the skin surface. The darkness of the pixels in the texture map image represents depth; i.e., the darker the pixel (the lower the pixel intensity) the deeper the skin texture at that pixel. The mean gray level of the flattened texture map image can be considered to represent the normal skin surface. Gray levels below the mean represent deeper features such as pores, fine-lines, wrinkles, scars, and the like. Gray levels above the mean represent raised features such as papules, pustules, whiteheads, and the like.

At 270, one or more metrics or scores can be generated based on the texture map, preferably as flattened at 260. One such metric is a texture score which is indicative of roughness. In exemplary implementations, such a score can be generated using a wavelet analysis procedure. In such a procedure, the flattened texture map is subjected to a two-dimensional wavelet transform. This yields the low-frequency component also known as the approximation and the high-frequency components, also known as the verticle, horizontal and diagonal details. Energy contents in these low- and high-frequency components can be calculated from the wavelet transform coefficients. In a second level transformation, the approximation can be further divided into low- and high-frequency components.

In exemplary implementations, three levels of wavelet transformations are performed on the texture map. For each level, a ratio of high-frequency energy to low-frequency energy is calculated as a measure of roughness at that level. A combination of the three ratios, such as the average thereof, can be generated as a roughness metric or score for the texture map.

The number of wavelet transformation levels used can be determined based on image resolution or the size of the features to be captured in the measurement. The high-frequency energy can be a sum of all three components: horizontal, vertical, and both vertical and horizontal directions, or can be selective, depending on the orientation and shape of the features of interest. For example, if one is only interested in measuring roughness due to pores, which are circular features (as opposed to wrinkles and fine lines), then the high-frequency energy only in the diagonal details is used. If only features of a certain size or range of sizes are of interest, then only one or two levels of wavelet tranformations can be used to generate a roughness metric.

While using the flattened texture map to generate roughness measurements may provide more accurate results, it is also possible to use the un-flattened texture map for this purpose. It has been observed that the un-flattened texture map may provide results that more closely comport with those of a human observer/grader, which may be preferable for some applications.

An average roughness measured among the wavelet transform levels used can be calculated and output at 280, such as by displaying alphanumerically, graphically or by any suitable means separately or together with the one or more input images, the texture map image, and/or the flattened texture map image. At 280, in addition to or as an alternative to displaying the texture roughness metric and/or images, the metric and/or images can be stored (such as in storage 150), communicated (such as over network 170), and/or processed further (such as by processor 140 or others.) Further processing may include, for example, performing wavelet transform based segmentation for detecting features such as pores and/or wrinkles. For example, the coefficients of diagonal details can be used for segmenting pores. The results of this processing can then be used, for example, to modify the standard image to highlight the features detected.

It should be noted that in addition or as an alternative to the above described texture measurements, a feature-specific texture measurement either based on the resolution of the images and feature of interest or based on the shape of the feature can also be generated using the techniques describe above. For example, round features such as pores, papules, and pustules will respond most to, or will contribute most in the wavelet transform diagonal details.

It should be also noted that in addition or as an alternative to the texture measurements generated as described above, other metrics for roughness can be generated, such as, for example: Ra, the arithmetic average of surface heights measured across a surface (i.e., the average the height across the microscopic peaks and valleys); maximum height (Ry); ten-point mean roughness (Rz); mean spacing of profile irregularities (Sm); mean spacing of local peaks of the profile (S) and profile bearing length ratio (tp); standard deviation in the gray-scale texture map intensity values; and area or fractional area of textural features, among others.

One or more of the metrics generated as described herein can be used to generate a photo-numeric scale for visual grading of skin roughness.

The use of techniques such as those described above in assessing the efficacy of treatments applied to skin will now be described with reference to FIGS. 5A-6B.

Figure 5B:
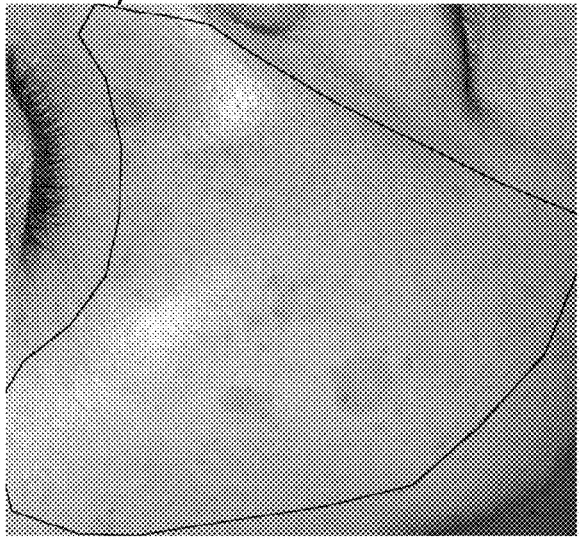
FIG. 5A shows a parallel-polarized baseline image of a portion of a subject's face and FIG. 5B shows a parallel-polarized follow-up image of the same portion of the subject's face.
Figure 5A:
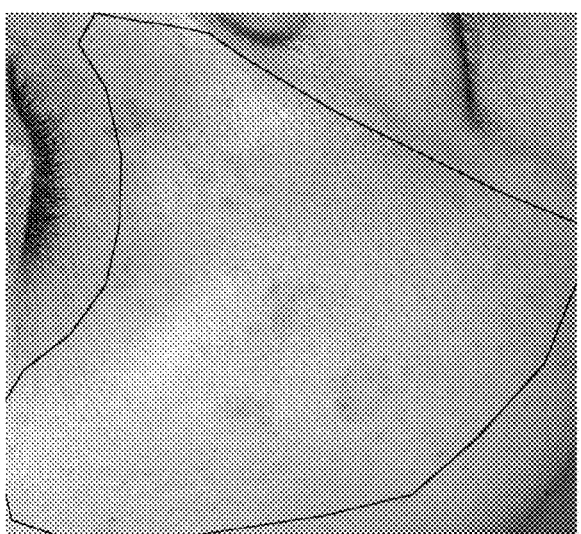

FIG. 5A shows a parallel-polarized image of a portion of a subject's face captured prior to treatment, representing a baseline condition. FIG. 5B shows a parallel-polarized image of the same portion of the subject's skin captured after treatment, such as topical skin tightening, for example.

Figure 6B:
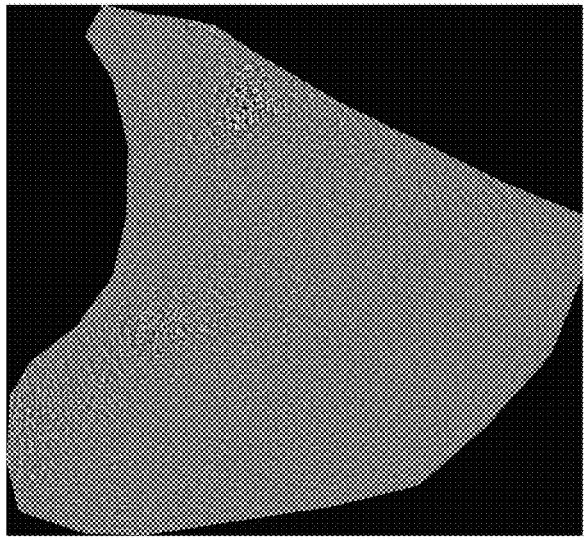
FIGS. 6A and 6B show texture map images generated in accordance with the above-described techniques, corresponding to the images of 5A and 5B, respectively.
Figure 6A:
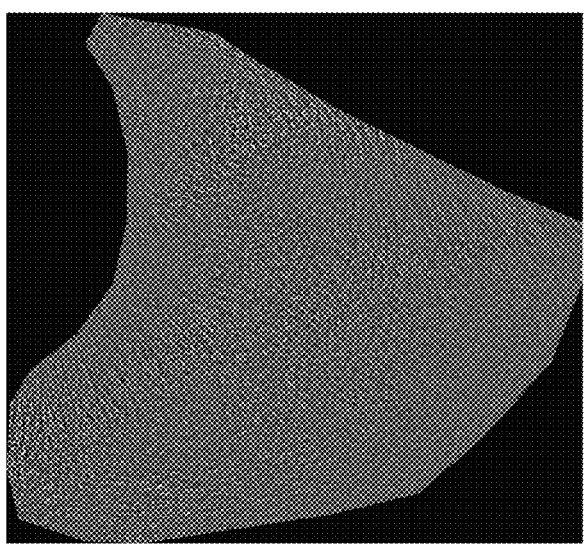

FIGS. 6A and 6B show texture map images generated in accordance with the above-described techniques, corresponding to the images of 5A and 5B, respectively. The texture map images of FIGS. 6A and 6B are limited to a selected region of interest 501 of the images of FIGS. 5A and 5B. The region 501 can be defined by user input or automatically generated based on facial features, such as the eyes, nose, lips, chin, ears, scalp, etc., and can be selected, for example, based on which portion of the subject's skin is treated. The use of such regions can help reduce and/or speed-up the processing entailed in generating texture maps by ignoring those skin areas that are not of interest, and help the user focus on those areas that are of interest.

Even though they are parallel-polarized images and thereby accentuate superficial features such as texture, it is difficult for an observer to discern the effects of the treatment by comparing the baseline image of FIG. 5A and the follow-up image of FIG. 5B. The effects of the treatment, however, are readily apparent in a comparison of the baseline texture map image of FIG. 6A and the follow-up texture map image of FIG. 6B.

In addition to providing a clear visual indication of treatment efficacy, a texture roughness percentage change between pre- and post-treatment texture maps can be generated, as described above, and displayed with the corresponding images and/or texture maps. For instance, the texture roughness percentage change of the follow-up texture map image of FIG. 6B relative to the baseline texture map image of FIG. 6A is 56.55%.

Texture maps as generated in accordance with the present disclosure can be used in other ways to further help visualize treatment efficacy by accentuating the changes in texture between baseline and follow-up images, as will now described with reference to FIGS. 7A-10B.

Figure 7A:
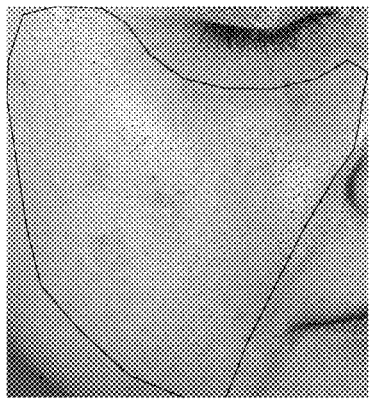
FIGS. 7A-10B show pairs of baseline and follow-up standard white light images modified so that pixels thereof corresponding to texture map pixels with values below a progressively greater threshold level are highlighted in a skin-contrasting color.
Figure 7B:
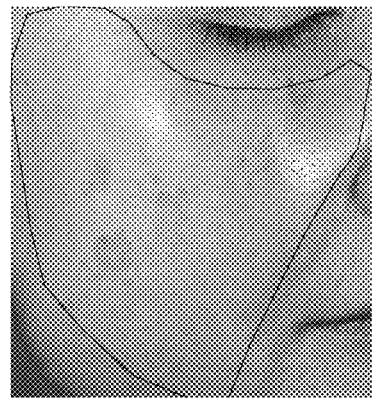

FIG. 7A is a standard white light image (corresponding to the baseline image of FIG. 5A) that has been modified by setting those pixels corresponding to pixels in the flattened texture map whose values fall below a first threshold level (L1) to a color, such as blue, which contrasts well with the surrounding skin. FIG. 7B shows a similarly modified standard white light image taken after treatment (corresponding to the follow-up image of FIG. 5B.)

Figure 8A:
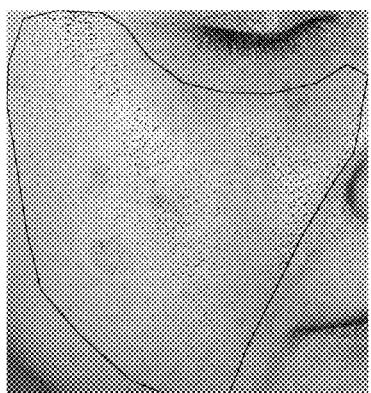
Figure 8B:
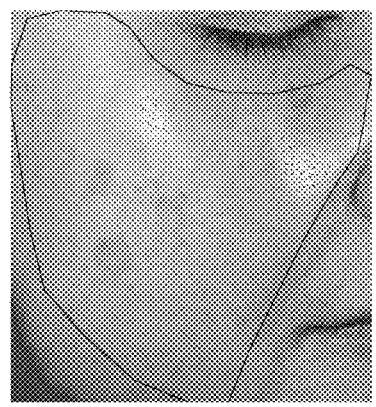
Figure 9A:
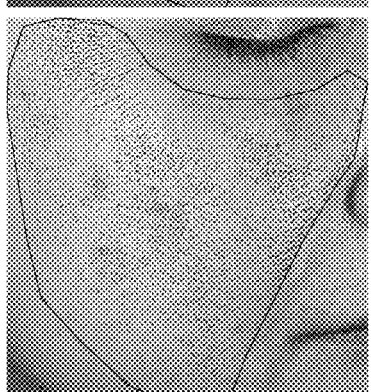
Figure 9B:
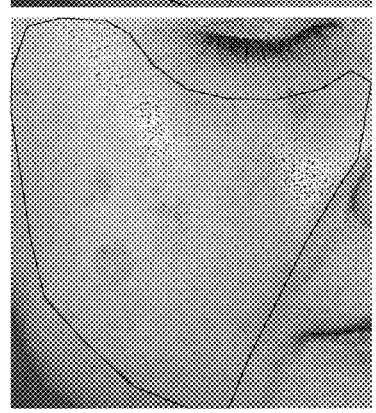
Figure 10A:
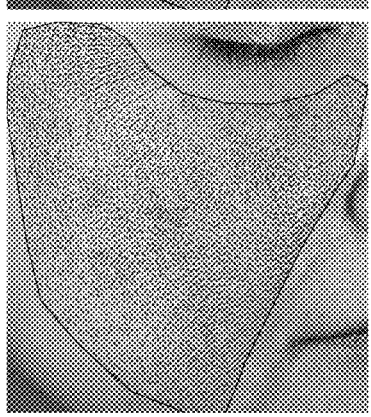
Figure 10B:
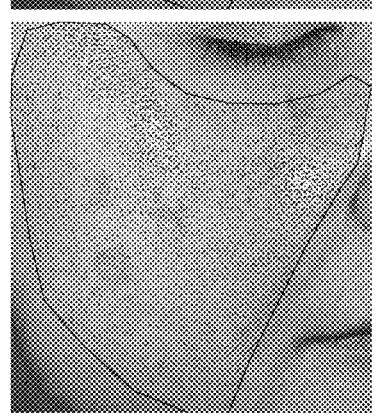

FIGS. 8A and 8B are the same baseline and follow-up standard white light images, respectively, similarly modified, but using a second threshold level (L2) greater than the first threshold level (L1). FIGS. 9A and 9B, show similarly modified images using a third threshold level (L3) and FIGS. 10A and 10B show similarly modified image using a fourth threshold level (L4), where L4>L3>L2>L1. In other words, in generating these successive pairs of images, the gray scale values of the texture maps shown in FIGS. 6A and 6B, are compared to successively increasing threshold levels, with L1 being the lowest (deepest) value to L4 being the greatest (shallowest) value. Those pixels in the standard white light images of FIGS. 7A-10A and 7B-10B corresponding to texture map gray scale values below the indicated threshold level are painted with the skin-contrasting color (e.g., blue).

In setting the levels L1-L4 used in the images of FIGS. 7A-10B, the average value of the flattened texture map is first determined. This value represents the normal surface level of the area of skin corresponding to the map, with lower values indicative of features below the normal surface level (such as wrinkles, fine lines and pores) and higher values indicative features above the normal surface level (such as papules and pustules). In an exemplary embodiment, the values of threshold levels L1-L4 are selected to be evenly distributed in the range between the average and minimum values of the flattened texture map.

Further threshold levels for values greater than the average value of the flattened texture map can also be determined and applied to modify one or more of the input images, similarly to those of FIGS. 7A-10B, to accentuate raised skin features; i.e., those features protruding above the normal surface level of the skin. Those pixels in the standard white light images corresponding to texture map gray scale values above the applied threshold level can be painted with a skin-contrasting color (e.g., red), preferably different than that used for features below the normal skin surface level.

A threshold level, such as the threshold levels (L1-L4) applied to generate images such as those of FIGS. 7A-10B, can be selected by a user, such as with a slider or other suitable UI control and the corresponding image pairs displayed side-by-side to provide the user with an interactive comparison between baseline and follow-up images, thereby graphically illustrating the effect of the treatment. In different implementations, the number of threshold levels can be greater or less than four, can be user-configurable, and/or can be set in accordance with other criteria (e.g., those levels below which given percentages of texture map pixel gray scale values will fall), among other alternatives.

Figure 11A:
FIGS. 11A and 11B show a further illustrative pair of baseline and follow-up standard white light images, respectively.
Figure 11B:
Figure 12A:
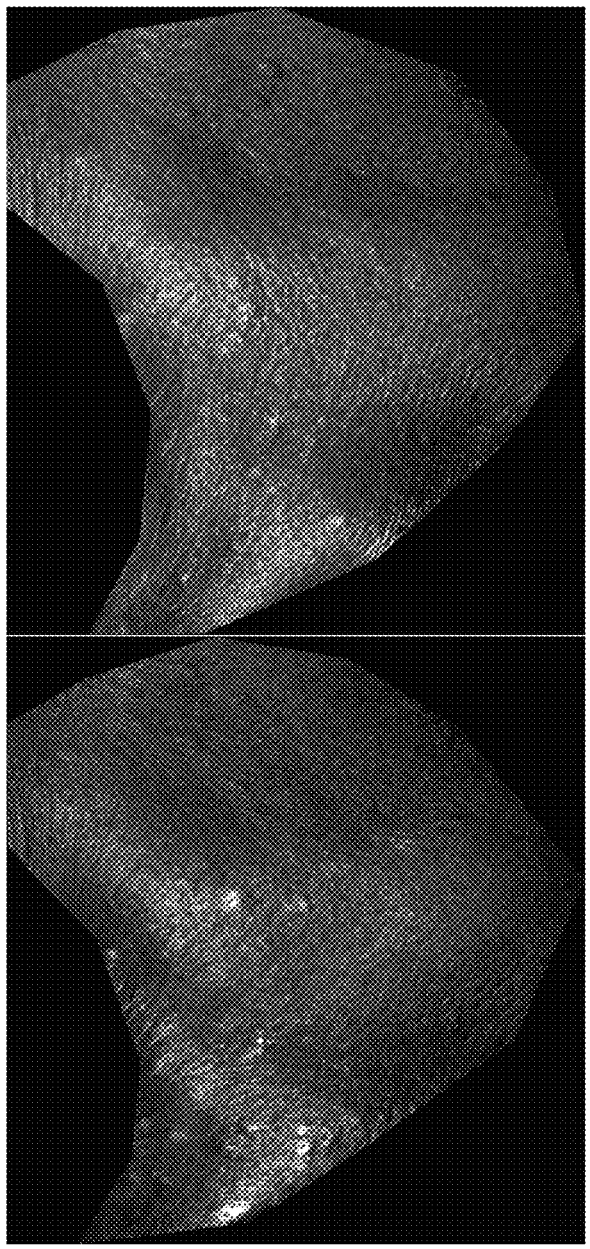
FIGS. 12A and 12B show texture map images corresponding to the images of FIGS. 11A and 11B, respectively.
Figure 12B:
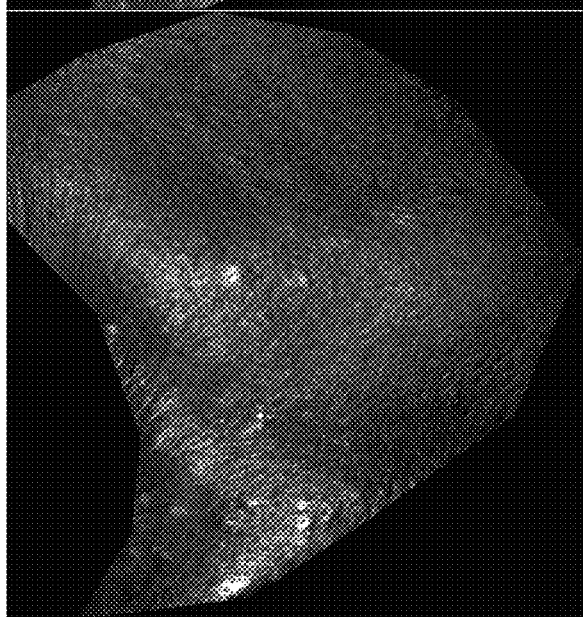

A further illustrative pair of baseline and follow-up images are shown in FIGS. 11A and 11B, respectively. Corresponding baseline and follow-up texture map images, generated in accordance with the present disclosure, are shown in FIGS. 12A and 12B, respectively. Additionally, a texture roughness score can be generated from the texture maps and displayed. In this example, the baseline texture roughness score is 0.5489 and the follow-up texture roughness score is 0.4909, representing a 10.57% reduction in texture roughness.

Unlike the skin area in the images of FIGS. 7A-10B, the skin area in the images of 11A-12B has raised features, such as papules and pustules. These features can be readily visualized in the texture map images of FIGS. 12A and 12B as bright spots. Moreover, similarly to FIGS. 7A-10B, the images of FIGS. 11A and 11B can be modified to accentuate raised and/or depressed features by coloring those pixels whose corresponding texture map values are above and/or below selected threshold levels.

In addition to measuring and evaluating treatment efficacy using before and after images and/or measurements, as described, implementations in accordance with the present disclosure can also be used in measurement-based treatment and/or making treatment suggestions, among other applications.

The foregoing merely illustrates principles of the present disclosure and it will thus be appreciated that those skilled in the art will be able to devise numerous alternative arrangements which, although not explicitly described herein, embody the principles of the present disclosure and are within its spirit and scope. For instance, as can be appreciated, a variety of arrangements of cameras and light sources are contemplated consistent with the present disclosure. In addition, while embodiments using white light illumination have been described, embodiments in accordance with the present disclosure may also be adapted for illumination of any suitable band or bands of wavelengths. Additionally, although illustrated as single elements, each such block or step shown may be implemented with multiple blocks or steps, or various combinations thereof. Also terms such as "software," "application," "program," "firmware," or the like, are intended to refer, without limitation, to any instruction or set of instructions, structure, or logic embodied in any suitable machine-readable medium. It is to be understood that numerous modifications may be made to the illustrative embodiments and that other arrangements may be devised without departing from the spirit and scope of the present invention as defined by the appended claims.

What is claimed is:
1. An apparatus comprising:
a storage device configured to store instructions; and
a processor configured to execute instructions stored in the storage device to:
obtain a parallel-polarized image of the skin area;
obtain a cross-polarized image of the skin area;
generate a texture map from a combination of the parallel-polarized and cross-polarized images;
generate at least one of a texture map image or a texture metric from the texture map; and cause the at least one of the texture map, the texture map image, or the texture metric to be displayed, stored, communicated, or processed.

2. The apparatus of claim 1, wherein the combination includes an intensity of the parallel-polarized image divided by an intensity of the cross-polarized image.

3. The apparatus of claim 1, wherein the processor is configured to execute instructions to perform an image registration operation on the parallel-polarized and cross-polarized images before generating the texture map.

4. The apparatus of claim 1, wherein the processor is configured to execute instructions to generate a flattened texture map.

5. The apparatus of claim 1, wherein generating the texture metric includes:
 applying a two-dimensional wavelet transform to the texture map to determine low- and high-frequency components, and
 determining a ratio of an energy of the high-frequency components to an energy of the low-frequency components.

6. The apparatus of claim 1, wherein generating the texture map image includes determining a gray scale value for each of a plurality of pixels of the texture map.

7. The apparatus of claim 1 comprising:
 an illumination source, wherein the illumination source is configured to illuminate the skin area with unpolarized light or polarized light of a first polarization orientation; and
 an image capture device configured to capture an image without polarization or with polarization of a second polarization orientation,
 wherein at least one of the first and second polarization orientations is selectable so that the polarization orientations are the same for capturing the parallel-polarized image of the skin area and mutually orthogonal for capturing the cross-polarized image of the skin area.

8. The apparatus of claim 1, wherein the processor is configured to execute instructions to detect a skin feature by performing a segmentation operation using at least one of the texture map or the texture map image.

9. The apparatus of claim 1, wherein the processor is configured to execute instructions to generate a further image by modifying one or more of the parallel-polarized or cross-polarized images, or a standard image in accordance with the texture map.

10. The apparatus of claim 1, wherein the processor is configured to execute instructions to generate at least one of a treatment evaluation or a treatment suggestion.

11. A method comprising:
 obtaining a parallel-polarized image of the skin area;
 obtaining a cross-polarized image of the skin area;
 generating a texture map from a combination of the parallel-polarized and cross-polarized images;
 generating at least one of a texture map image or a texture metric from the texture map; and
 causing the at least one of the texture map, the texture map image, or the texture metric to be displayed, stored, communicated, or processed.

12. The method of claim 11, wherein the combination includes an intensity of the parallel-polarized image divided by an intensity of the cross-polarized image.

13. The method of claim 11 comprising performing an image registration operation on the parallel-polarized and cross-polarized images before generating the texture map.

14. The method of claim 11, comprising generating a flattened texture map.

15. The method of claim 11, wherein generating the texture metric includes:
 applying a two-dimensional wavelet transform to the texture map to determine low- and high-frequency components, and
 determining a ratio of an energy of the high-frequency components to an energy of the low-frequency components.

16. The method of claim 11, wherein generating the texture map image includes determining a gray scale value for each of a plurality of pixels of the texture map.

17. The method of claim 11 comprising:
 illuminating the skin area with unpolarized light or polarized light of a first polarization orientation; and
 capturing an image without polarization or with polarization of a second polarization orientation,
 wherein at least one of the first and second polarization orientations is selectable so that the polarization orientations are the same for capturing the parallel-polarized image of the skin area and mutually orthogonal for capturing the cross-polarized image of the skin area.

18. The method of claim 11 comprising detecting a skin feature by performing a segmentation operation using at least one of the texture map or the texture map image.

19. The method of claim 11 comprising generating a further image by modifying one or more of the parallel-polarized or cross-polarized images, or a standard image in accordance with the texture map.

20. A non-transitory computer readable storage medium containing instructions for execution by a processor for carrying out the method of claim 11.

* * * * *